(12) United States Patent  (10) Patent No.: US 7,729,523 B2
Hammond  (45) Date of Patent: Jun. 1, 2010

(54) METHOD AND SYSTEM FOR VIEWING IMAGE DATA

(75) Inventor: Christopher Reynolds Hammond, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 1322 days.

(21) Appl. No.: 11/018,672

(22) Filed: Dec. 21, 2004

(65) Prior Publication Data

US 2006/0133659 A1     Jun. 22, 2006

(51) Int. Cl.
*G06K 9/00* (2006.01)

(52) U.S. Cl. .............................. 382/128; 128/922; 378/4

(58) Field of Classification Search ................. 382/100, 382/128, 130, 131, 132, 133; 128/922; 378/4–27
See application file for complete search history.

(56) References Cited

U.S. PATENT DOCUMENTS

| | | | |
|---|---|---|---|
| 4,945,476 A * | 7/1990 | Bodick et al. ............... 600/301 |
| 6,873,717 B2 * | 3/2005 | Lure et al. ................... 382/128 |
| 7,027,633 B2 * | 4/2006 | Foran et al. .................. 382/133 |
| 7,295,691 B2 * | 11/2007 | Uppaluri et al. ............. 382/130 |
| 2001/0040589 A1 * | 11/2001 | De Bliek et al. ............ 345/700 |
| 2002/0028006 A1 | 3/2002 | Novak et al. ................. 382/128 |
| 2004/0120558 A1 * | 6/2004 | Sabol et al. .................. 382/128 |
| 2004/0120580 A1 | 6/2004 | Sabol et al. .................. 382/224 |
| 2005/0043966 A1 * | 2/2005 | Harnsberger et al. ........... 705/2 |
| 2005/0096530 A1 * | 5/2005 | Daw et al. ................... 600/408 |

FOREIGN PATENT DOCUMENTS

EP  1365345 A2  11/2003
WO  WO 01/59687 A1  8/2001

* cited by examiner

*Primary Examiner*—Anand Bhatnagar
(74) *Attorney, Agent, or Firm*—Patrick N. Patnode (57) ABSTRACT

A technique is provided for viewing image data via a user interface. The technique includes displaying two or more selectable tabs and displaying a corresponding analysis for a selected tab. Each tab corresponds to an analysis of a set of radiological images and the corresponding analysis comprises one or more identified features. The technique also includes displaying a corresponding image for a selected feature such that the selected feature is visually indicated on the corresponding image.

20 Claims, 7 Drawing Sheets

METHOD AND SYSTEM FOR VIEWING IMAGE DATA

BACKGROUND

The invention relates generally to image display techniques and in particular to the display of multiple analyses in conjunction with images.

Various technical fields engage in some form of image evaluation and analysis for monitoring or diagnostic purposes. For example, medical imaging technologies produce various types of diagnostic images which a doctor or radiologist may review for the presence of identifiable features of diagnostic significance, such as lesions, calcifications, nodules, and so forth. Similarly, in other fields, other features may be of interest. For example, non-invasive imaging of package and baggage contents, analysis of satellite image data, evaluation of astronomical and geological image data and others may similarly be reviewed to identify and classify recognizable features. With the development of digital imaging and image processing techniques, the quantity of image data requiring analysis in many of these technical fields has increased substantially.

The increased amount of available image data may require a large number of trained human technologists to process the data. Because the number of qualified technologists available at a given time may be limited, computer implemented techniques may be employed to provide valuable assistance and timesavings to the reviewing technologists. For example, computer assisted detection and/or diagnosis (CAD) algorithms have been developed to supplement and assist review and analysis of many types of image data, including medical image data. In addition, in some contexts, such as the review of medical image data, more than one independent assessment and analysis of a set of image data may be desirable to improve accuracy and to assure quality control. It may, however, be difficult to intuitively and easily combine the separate independent readings from different technologists or computerized routines into a final form that may be easily and quickly reviewed.

It is, therefore, desirable to provide an efficient and improved user interface allowing a reviewer to quickly and easily view the separate and combined analysis results generated by different readers and/or computer implemented routines.

BRIEF DESCRIPTION

Briefly in accordance with one aspect of the technique, a method is provided for viewing image data. The method provides for displaying two or more selectable tabs and displaying a corresponding analysis for a selected tab. Each tab corresponds to an analysis of a set of radiological images and the corresponding analysis comprises one or more identified features. The method further provides for displaying a combined tab. The combined tab corresponds to a combined presentation of two or more separate analysis of the set of radiological images of the patient. The method also provides for displaying a corresponding image for a selected feature such that the selected feature is visually indicated on the corresponding image. Systems and computer programs that afford functionality of the type defined by this method may be provided by the present technique.

In accordance with another aspect of the technique, an image viewing station is provided. The image viewing station includes a computer configured to display a user interface comprising of a viewable area. The viewable area includes a first portion configured to display two or more selectable tabs and a second portion configured to display a corresponding analysis for a selected tab. Each tab corresponds to an analysis of a set of radiological images and the corresponding analysis comprises one or more identified features. The viewable area also includes a third portion configured to display a corresponding image for a selected feature such that the selected feature is visually indicated on the corresponding image. The viewable area further includes a fourth portion configured to display a selectable combined tab. The combined tab corresponds to a combined presentation of two or more separate analysis of the set of radiological images of the patient.

In accordance with a further aspect of the present technique, a user interface comprising of a viewable area is provided. The viewable area includes a first portion configured to display two or more selectable tabs and a second portion configured to display a corresponding analysis for a selected tab. Each tab corresponds to an analysis of a set of radiological images and the corresponding analysis comprises one or more identified features. The viewable area also includes a third portion configured to display a corresponding image for a selected feature such that the selected feature is visually indicated on the corresponding image. The viewable area further includes a fourth portion configured to display a selectable combined tab. The combined tab corresponds to a combined presentation of two or more separate analysis of the set of radiological images of the patient.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present technique is generally directed to the display of multiple image analyses in conjunction with the respective images. Such display techniques may be useful in a variety of imaging contexts, such as CT imaging, X-ray radiography, industrial inspection systems, nondestructive testing, heavy metals analysis and others. Though the present discussion provides examples in a medical imaging context, one of ordinary skill in the art will readily apprehend that the application of these techniques in non-medical imaging contexts, such as for industrial imaging, security screening, analysis of satellite and radar weather data and/or evaluation of astronomical and geological data, is well within the scope of the present techniques.

Figure 1:
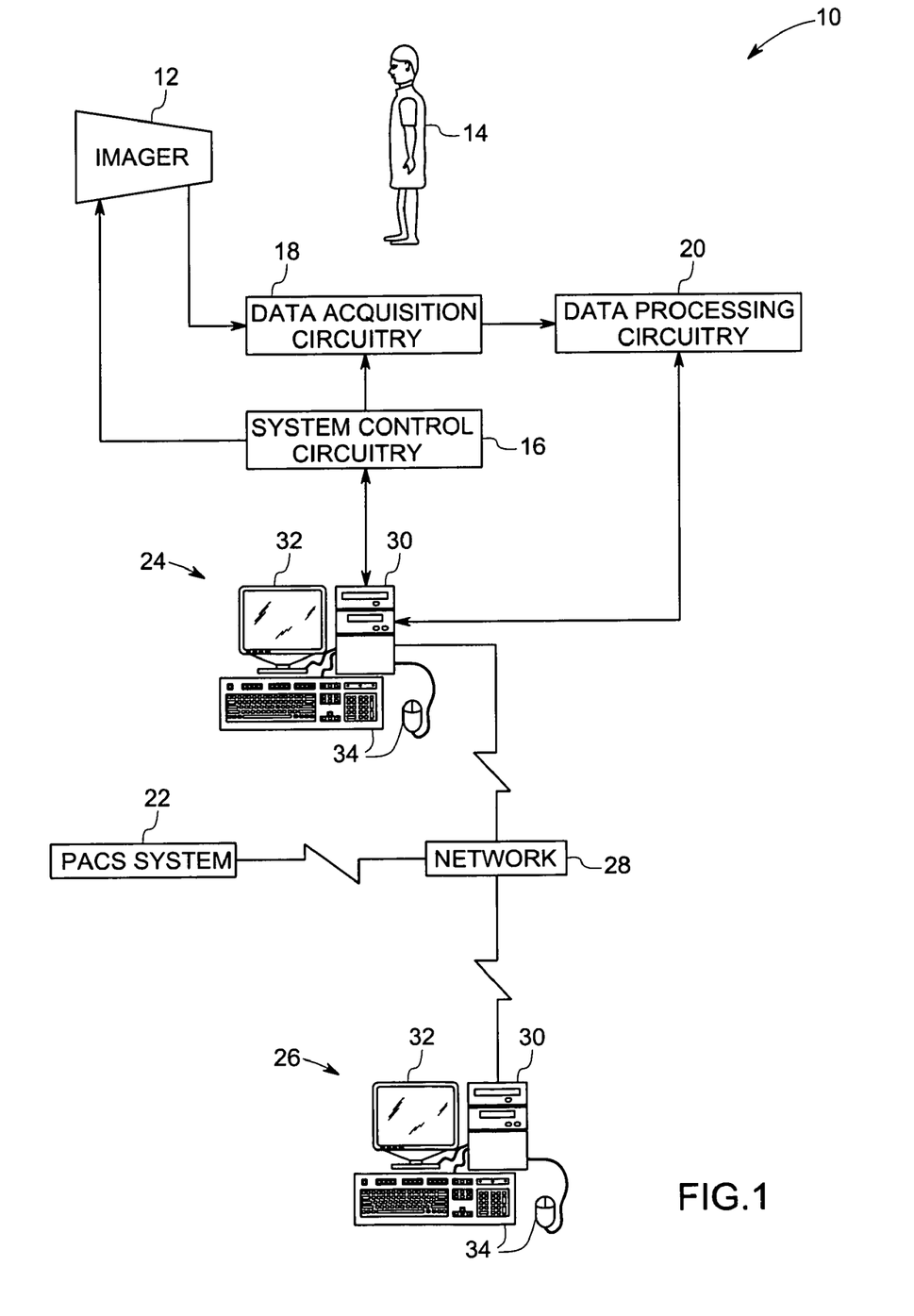
FIG. 1 depicts an exemplary imaging system in accordance with one aspect of the present technique.

Turning now to the drawings, and referring first to FIG. 1, an exemplary imaging system 10 suitable for use in a medical context is depicted. Generally, the imaging system 10 includes some type of imager 12 that may operate in accordance with various physical principles for creating image data. In general, the imager 12 creates image data representative of regions of interest in a patient 14 either in a conventional support, such as photographic film, or in a digital medium.

In the depicted embodiment, the imager 12 operates under the control of system control circuitry 16. The system control circuitry 16 may include a wide range of circuits, such as radiation source control circuits, timing circuits, circuits for coordinating data acquisition in conjunction with patient or table movements, circuits for controlling the position of radiation sources and detectors, and so forth. In the present context, the system control circuitry 16 may also include memory elements for storing programs and routines implementing the techniques described herein which may be executed by the system control circuitry 16 or by associated components of the imaging system 10.

The imager 12, following acquisition of the image data or signals, may process the signals, such as for conversion to digital values, and forward the image data to data acquisition circuitry 18. In the case of analog media, such as photographic film, the data acquisition system may generally include supports for the film, as well as equipment for developing the film and producing hard copies that may be subsequently digitized. For digital systems, the data acquisition circuitry 18 may perform a wide range of initial processing functions, such as adjustment of digital dynamic ranges, smoothing or sharpening of data, as well as compiling of data streams and files, where desired. The data may then be transferred to data processing circuitry 20 where additional processing and analysis are performed. For conventional media such as photographic film, the data processing system may apply textual information to films, as well as attach certain notes or patient-identifying information. For the various digital imaging systems available, the data processing circuitry 20 perform substantial analyses of data, ordering of data, sharpening, smoothing, feature recognition, and so forth, which facilitate the generation of a useful set of image data. The data processing functions may be performed, in general, under the guidance of one or more technologists. The acquired images or image data may be stored in short or long-term storage devices, such as a picture archiving communication system (PACS) 22.

The above-described operations and functions of the imaging system 10 may be controlled by a scanner console 24, which typically interfaces with the system control circuitry 16. The scanner console 24 may include one or more general purpose or application specific computers 30 or processor-based components. The scanner console 24 may include a monitor 32 or other visual display and one or more input devices 34. The monitor 32 and input devices 34 may be used for viewing and inputting configuration information or for operating aspects of the imaging system 10, in accordance with the techniques discussed herein. As with the system control circuitry 16, the scanner console 24 may comprise or communicate with a memory or data storage component for storing programs and routines implementing the techniques described herein which may be executed by the scanner console 24 or by associated components of the imaging system 10. Moreover, the memory or storage component may comprise one or more memory devices, such as magnetic or optical drives, of similar or different types, which may be local or remote from one another.

It should be noted that more than one scanner console 24 may be provided. For example, an imaging scanner or station may include a console which permits regulation of the parameters involved in the image data acquisition procedure, whereas a different scanner console, such as a viewing station, may be provided for manipulating, enhancing, viewing, and analyzing images reconstructed from data acquired by the imager 12.

In such an embodiment, a remote viewing station or console 26 may communicate with other components of the imaging system 10, such as via a network 28. As will be appreciated by those skilled in the art, any suitable circuitry, such as modems, servers, firewalls, VPN's and so forth may be included within the network 28. For example, the network 28 may include one or more of a local intranet within the medical facility, a service network between the facility and a service provider, a direct communication line between the local and remote components of the collaborative imaging system 10, a virtual private network established over the Internet, the Internet itself, and so forth.

The remote viewing station or console 26 may comprise many, if not all, of the components of the scanner console 24, such as a monitor 32 and input devices 34. The remote console 26 allows a remote operator to access other elements of the imaging system 10 via the network 28. For example, the remote console 26 may comprise a PACS workstation or other interface that may be used to access the stored or acquired image data from a remote location. As such, the remote console 26 may be used by a technologist who may assist in the processing of acquired imaging data, a radiologist who reads the acquired or processed imaging data, a referring physician who refers to the analyzed images for patient consultation, and so forth. Alternatively, a computer assisted detection and/or diagnosis (CAD) algorithms or an automated algorithm may be employed at scanner console 24 or remote console 26 to analyze the acquired or processed imaging data.

Figure 2:
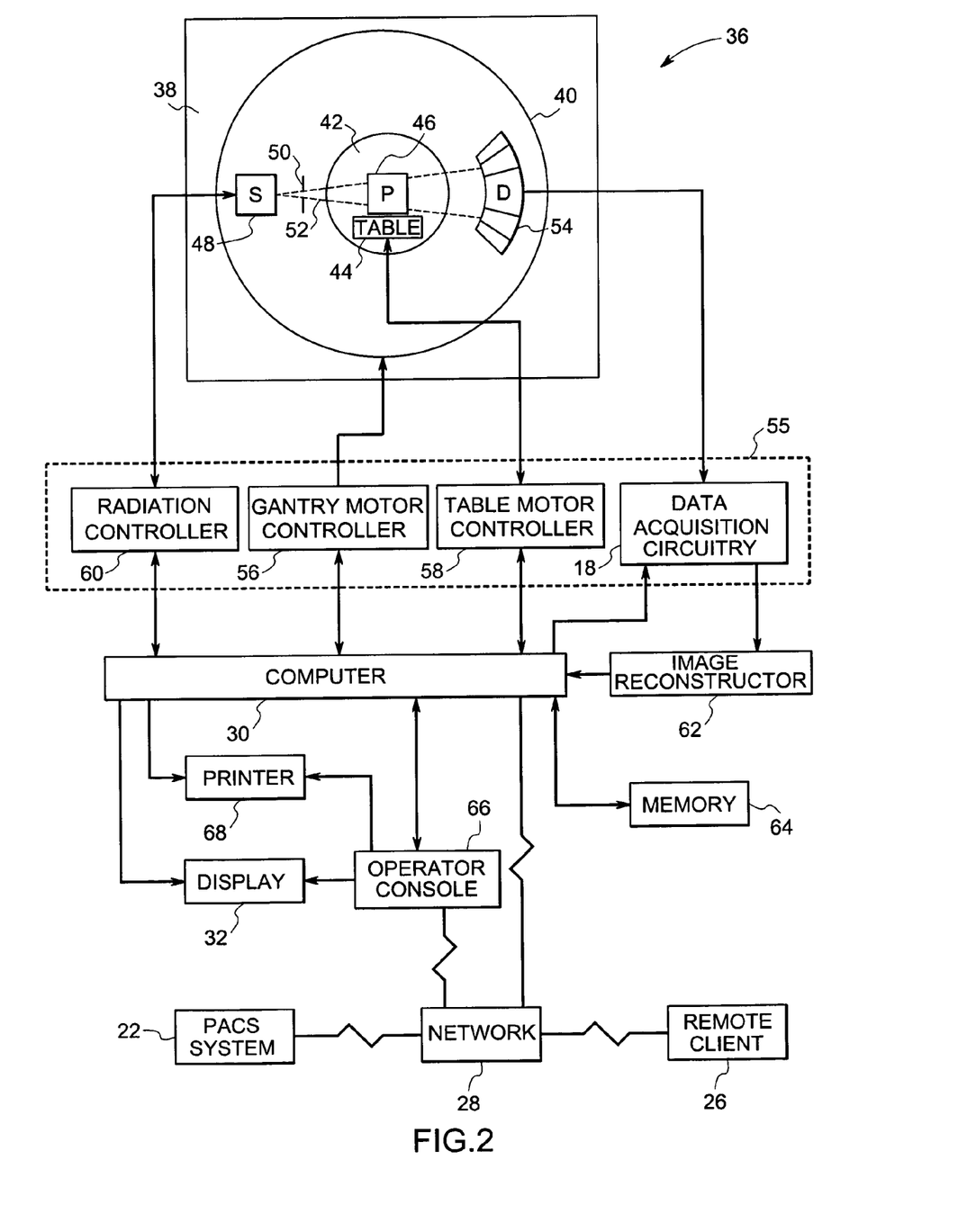
FIG. 2 depicts an exemplary CT imaging system in accordance with one aspect of the present technique.

While FIG. 1, depicts a generalized exemplary imaging system 10 for use in accordance with the present technique, FIG. 2 depicts particular embodiment of the generalized system of FIG. 1 as an example. In particular, FIG. 2, depicts an exemplary computed tomography (CT) system designed both to acquire and process original image data for display and analysis in accordance with the present technique. The CT imaging system 36 is illustrated with a frame 38 and a gantry 40 that has an aperture (imaging volume or CT bore volume) 42. A patient table 44 is positioned in the aperture 42 of the frame 38 and the gantry 40. The patient table 44 is adapted so that a patient 46 may recline comfortably during the examination process.

The gantry 40 includes an X-ray source 48 positioned adjacent to a collimator 50. The collimator 50 typically defines the size and shape of an X-ray beam 52 that emerges from the X-ray source 48. In typical operation, the X-ray source 48 projects X-rays 52 towards detector 54 mounted on the opposite side of the gantry 40. Collimator 50 permits the X-ray beam 52 to pass into a particular region in which a subject, such as a human patient 46 is positioned. It should be noted that the particular region of the patient 46, for instance the liver, lungs, pancreas and so on, is typically chosen by an operator so that the most useful scan of a region may be acquired.

A portion of the radiation 52 passes through or around the subject and impacts the detector array 54. The detector array 54 may be a single slice detector or a multi-slice detector and is generally formed by a plurality of detection elements. Each detector element produces an electrical signal that represents the intensity of the incident X-ray beam 52 at the detector element when the beam 52 strikes the detector array 54. These signals are acquired and processed to reconstruct an image of the features within the subject 46.

Furthermore, the gantry 40 may be rotated around the subject 46 so that a plurality of radiographic views may be collected along an imaging trajectory described by the motion of the X-ray source 48 relative to the patient 46. In particular, as the X-ray source 48 and the detector array 54 rotate along with the CT gantry 40, the detector array 54 collects data of X-ray beam attenuation at the various view angles relative to the patient 46. The X-ray attenuation data may then be processed to generate one or more images of the internal structures within the scanned area of the patient 46.

Rotation of the gantry 40 and operation of the source 48 and table 44 is controlled by a CT system controller 55. In the illustrated embodiment, the system controller 55 may include a gantry motor controller 56 that controls the rotational speed and position of the gantry 40. The system controller 55 may further include a table motor controller 58 that controls the linear displacement of the motorized table 44 within the CT bore volume 42. Additionally, the depicted system controller 55 includes an X-ray controller 60 to control the X-ray source 48. Particularly, the X-ray controller 60 may be configured to provide power and timing signals to the X-ray source 48.

Further, the depicted system controller 55 may include data acquisition circuitry 18. In this exemplary embodiment, the detector array 54 is coupled to the system controller 55, and more particularly to the data acquisition circuitry 18. The data acquisition circuitry 18 typically receives sampled analog signals from the detector array 54 and converts the data to digital signals for subsequent processing. An image reconstructor 62 coupled to the computer 30 receives sampled and digitized data from the data acquisition system 18 and performs high-speed image reconstruction. Alternatively, reconstruction of the image may be done by hardware and/or software included in the computer 30. Once reconstructed, the image produced by the CT imaging system 36 reveals internal features of the patient 46.

The data collected by the data acquisition system 18 or the reconstructed images may be transmitted to the computer 30 and moreover, to a memory 64. It should be understood that any type of memory to store a large amount of data may be utilized by such an exemplary imaging system 36. The computer 30 is typically used to control the CT system 36 and may be adapted to control features enabled by the system controller 16. The computer 30 in turn may be configured to receive commands and scanning parameters from an operator via an operator console 66.

A display 32 coupled to the operator console 66 and/or the computer 30 may be utilized to observe the reconstructed image and to control imaging. Additionally, the scanned image may also be printed on to a printer 68 which may be coupled to the computer 30 and/or the operator console 66. Further, as described earlier, the computer 30 and/or operator console 66 may also be coupled to a picture archiving and communications system (PACS) 22 via a network 28. It should be noted that the computer 30 and/or operator console 64 may also be coupled to a remote system 26, such as radiology department information system (RIS), hospital information system (HIS) or to an internal or external network, so that others at different locations may gain access to the image and to the image data.

Figure 3:
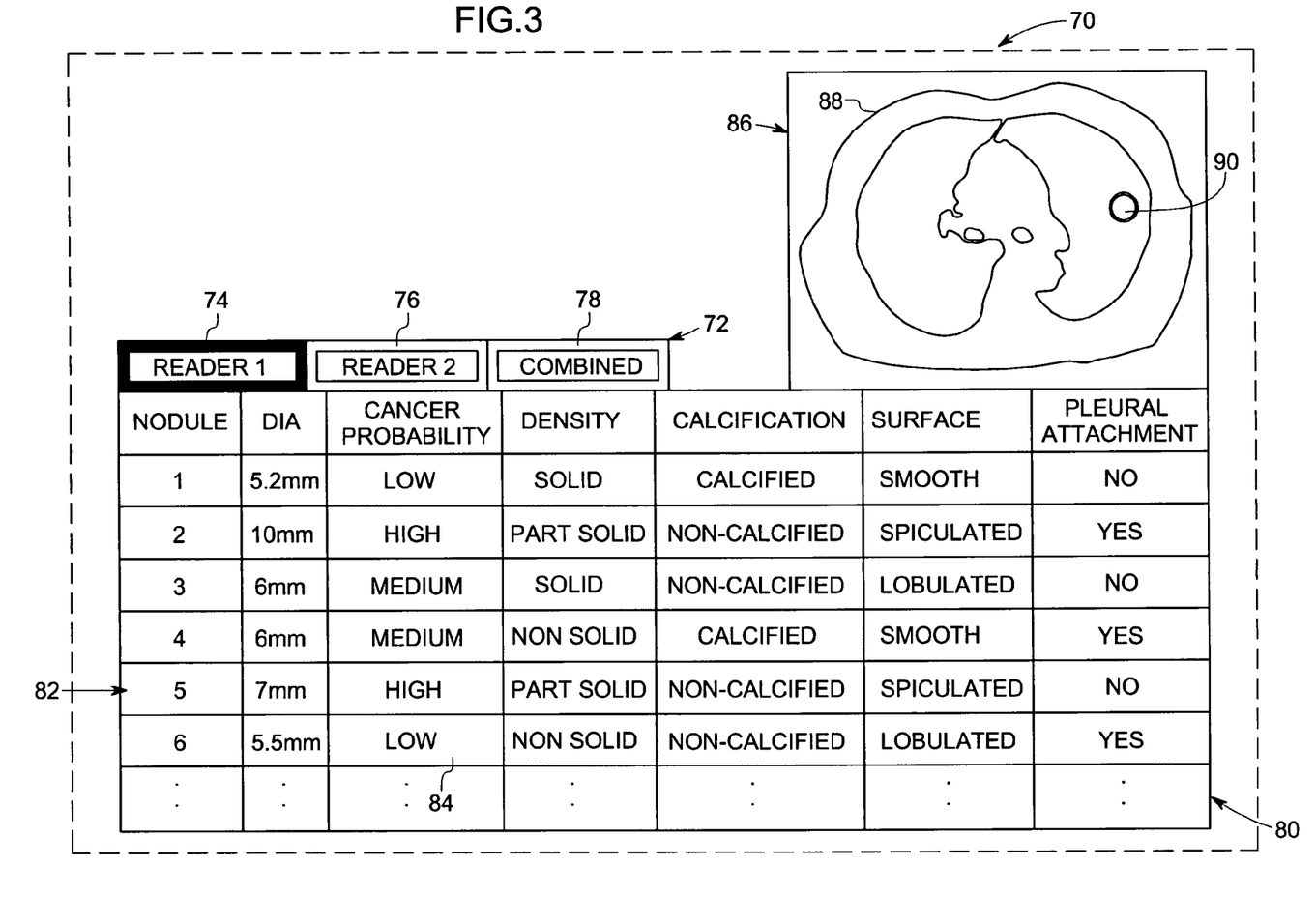
FIG. 3 depicts an exemplary user interface for displaying multiple analyses of a set of radiological images in accordance with one aspect of the present technique.

The image data acquired and displayed by the imaging system 10 and the CT imaging system 36 may be reviewed by multiple clinicians and/or automated routines during the course of an examination. It may be desirable to display the results of these various analyses, particularly in conjunction with the relevant images, such that all of the analyses are readily available. For example, referring now to FIG. 3, a user interface 70 for displaying an analysis of a set of radiological images is depicted. The user interface 70 simultaneously displays a radiological image from a set of images and a corresponding analysis of the images. In the depicted embodiment, a set 72 of selectable tabs is provided in the viewable area, where each tab corresponds to an individual, combined or historical analysis of the set of radiological images. For example, the "reader 1" tab 74 (as illustrated in FIG. 3) may correspond to the analysis performed by a first reader (such as a radiologist, clinician, or CAD routine) while the "reader 2" tab 76 may correspond to a second analysis performed by a second reader. Similarly, the "combined" tab 78 may correspond to a combination of two or more of the analyses available for display.

Figure 4:
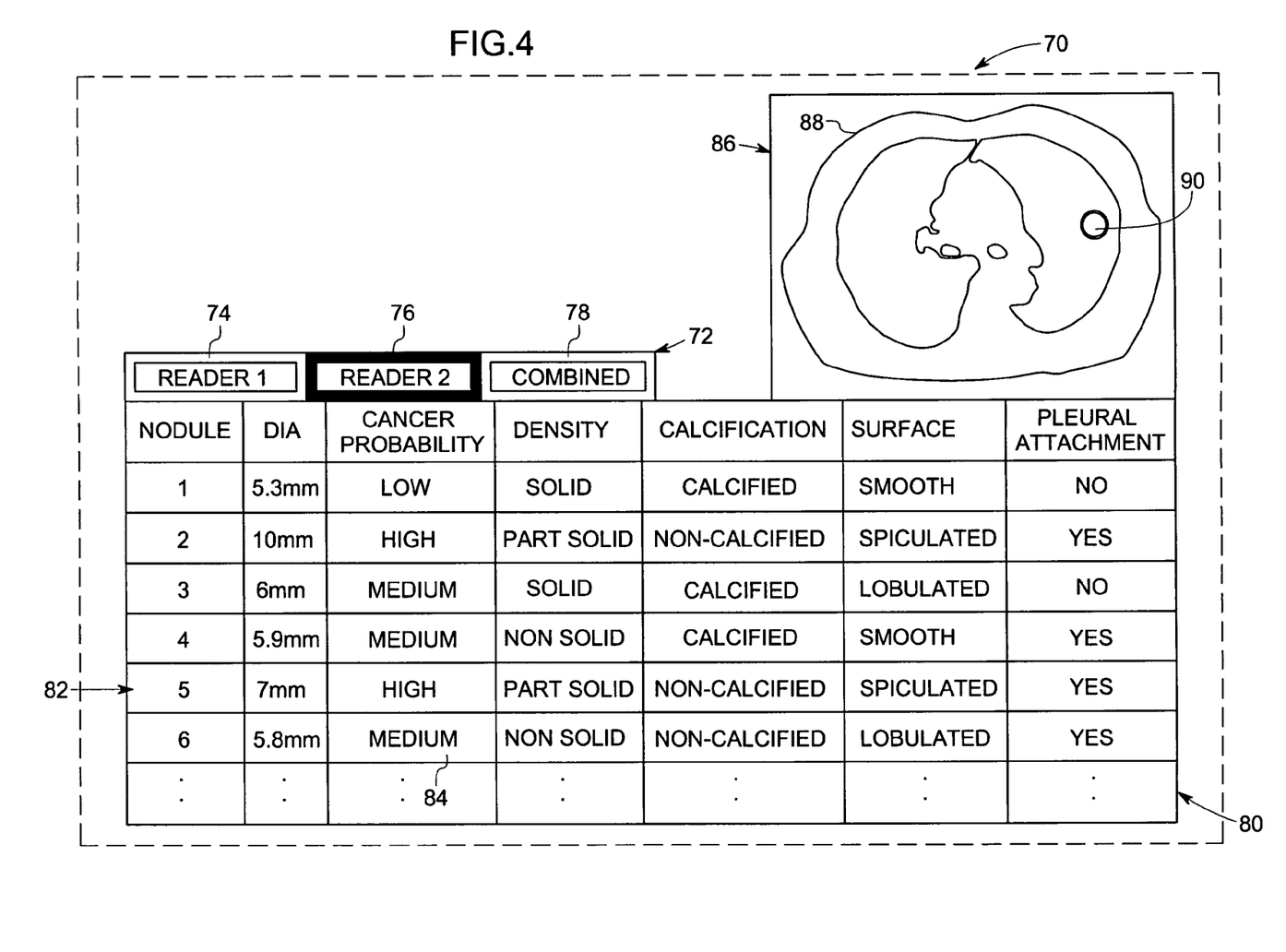
FIG. 4 depicts the exemplary user interface of FIG. 3 configured to display the analysis a second reader in accordance with one aspect of the present technique.

The viewable area also includes an analysis display area 80 for displaying the analysis corresponding to the selected tab. An analysis of a set of radiological images corresponding to a selected tab includes one or more feature 82, such as the listed nodules, identified in one or more of the images. Each identified features 82 may be associated with one or more feature characteristics 84, such as diameter of the nodule, cancer probability, density, presence of calcification, type of surface, pleural attachment and so forth, which are typically measured or provided by the human or computer reader generating the analysis. For example, an analysis comprising the features 82 identified by "reader 1 and the associated feature characteristics 84, is illustrated in FIG. 3 when "reader 1" tab 74 is selected. Similarly, FIG. 4 depicts an analysis generated by a second reader which is displayed when the "reader 2" tab 76 is selected. As will be appreciated by those of ordinary skill in the art, the features 82 identified by each reader may differ, such that the different analysis may include some identified features 82 in common and other features 82 which are identified only in one or some of the analyses. Likewise, the quantities or qualities provided for feature characteristics 84 of common features 82 may vary between the different analyses in which they are identified. For example, two readers may identify the same feature in their respective analyses but assign different measures, probabilities, qualities, and so forth to the commonly identified feature 82. For example, referring now to FIG. 3 and FIG. 4, the feature characteristics 84 associated with diameter and cancer probability of "nodule 6" differ for each reader. As will be appreciated by those of ordinary skill in the art, in this and other examples herein, the identification of a common feature 82 with a common numeric identifier is for convenience and simplicity. In practice, different readers will not necessarily identify common features 82 in the same order. Likewise, differences in what readers identify as features 82 may result in the assignment of different reference characters to common features in different analyses. For the sake of simplicity, however, common features will be denoted by common numeric identifiers herein.

Returning now to FIG. 3, the viewable area further includes an image display region 86 where an image 88 corresponding to a selected feature is displayed. For example, if "nodule 1" is selected by the viewer, the image of the set of radiographic images in which "nodule 1" was identified is displayed. In addition, as depicted in FIG. 3, the selected feature is visually indicated in the displayed image 88 using a visual indicator, such as a color enhancement or a marker. For example, in FIG. 3, an indicator reticle 90 is displayed in the image 88 such that it generally encircles a selected feature 82. Alternatively, the selected feature 82 may be enhanced in the image 88 via a computer or digital enhancement routine. For example, upon selection of a feature 82, the corresponding portion of the displayed image 88 may be enlarged, filtered, sharpened, contrast enhanced, or otherwise visually enhanced to allow easier or improved review by the viewer.

With the above discussion in mind, referring once again to FIG. 3, it can be seen that the features 82 and feature characteristics 84 are displayed in a tabular format, such as a table or spreadsheet, such that each line of the analysis represents one feature and its associated characteristics. A viewer may navigate this interface using an input device, such as a mouse, keyboard, digital stylus, and so forth. For example, selecting a tab 74 results in the corresponding analysis (comprising the identified features 82 and feature characteristics 84) being displayed. Selection of an identified feature 82 in the displayed analysis results in the display of the corresponding image 88 and a visual indication, such as via indicator reticle 90, of the selected feature 82. Alternatively, selection of a visual indicator 90 in the displayed image 88 may result in the corresponding feature 82 and feature characteristics 84 being visually indicated, such as by color, marker, line weighting, and so forth.

In the user interface depicted in FIG. 3 and subsequent figures, respective areas allocated to display of the analyses and the image 88 are adjustable relative to one another. In one embodiment, the user interface components may interact with one another to allow the user to update and review the selected features 82 and corresponding feature characteristics 84 via image processing and data entry routines residing in the computer. These routines may be activated by the user through one or more input devices such as keyboard, mouse and so forth.

Figure 5:
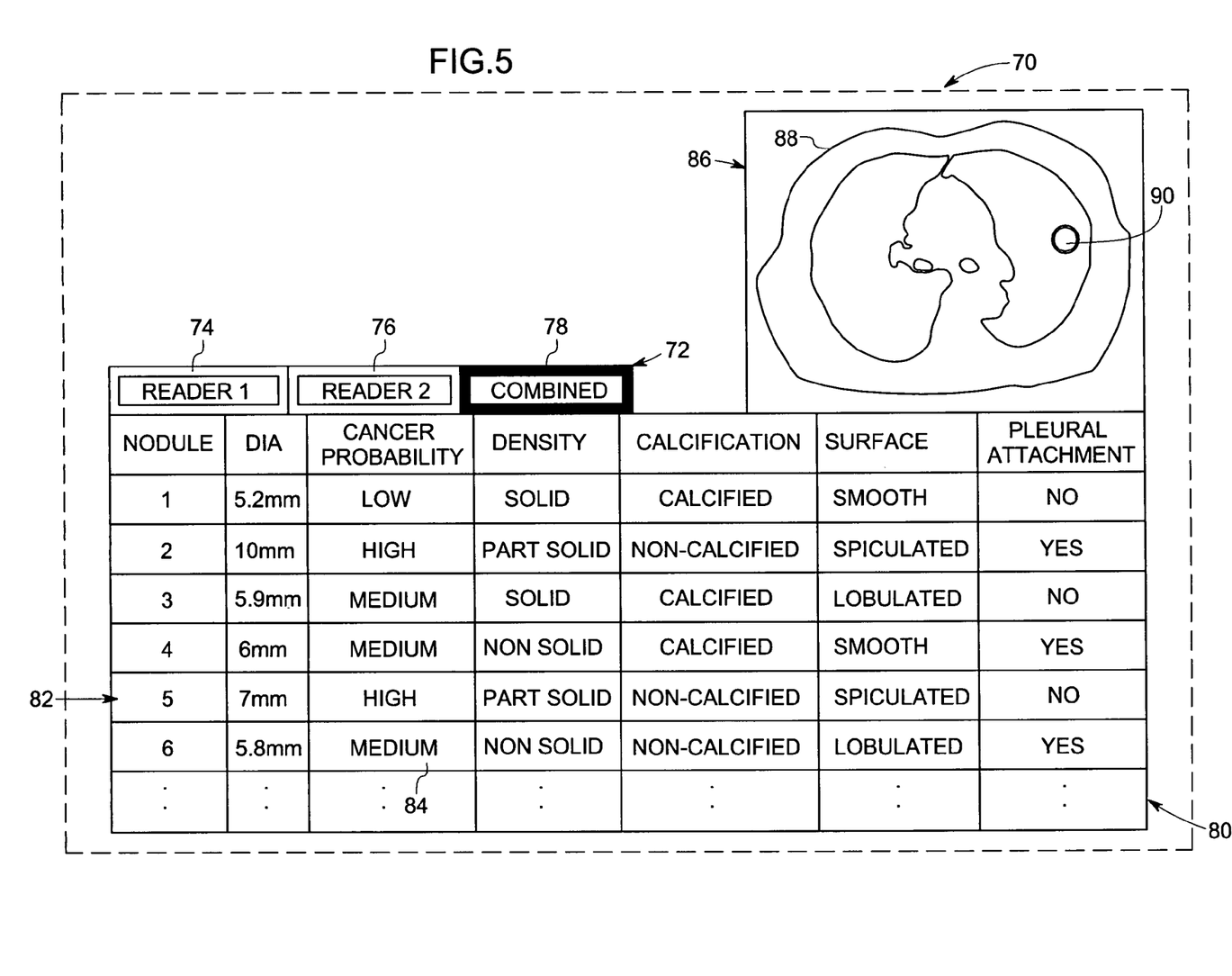
FIG. 5 depicts the exemplary user interface of FIG. 3 configured to display a combined analysis in accordance with one aspect of the present technique.

While FIGS. 3 and 4 have discussed the review of separate analyses by a viewer, FIG. 5 depicts a combined analysis, such as may be selected by review via the "combined" tab 78 of the depicted interface. In this embodiment, the selectable "combined" tab 78 displays a combined presentation of two or more separate analyses of the set of radiological images generated by two or more different readers. In this embodiment, selection of the "combined" tab 78 allows a viewer to compare the textual analyses in a side-by-side manner while also viewing the image data itself. Additional selectable tabs 92 may be provided as desired to achieve the desired grouping of analyses under the respective tabs.

Figure 6:
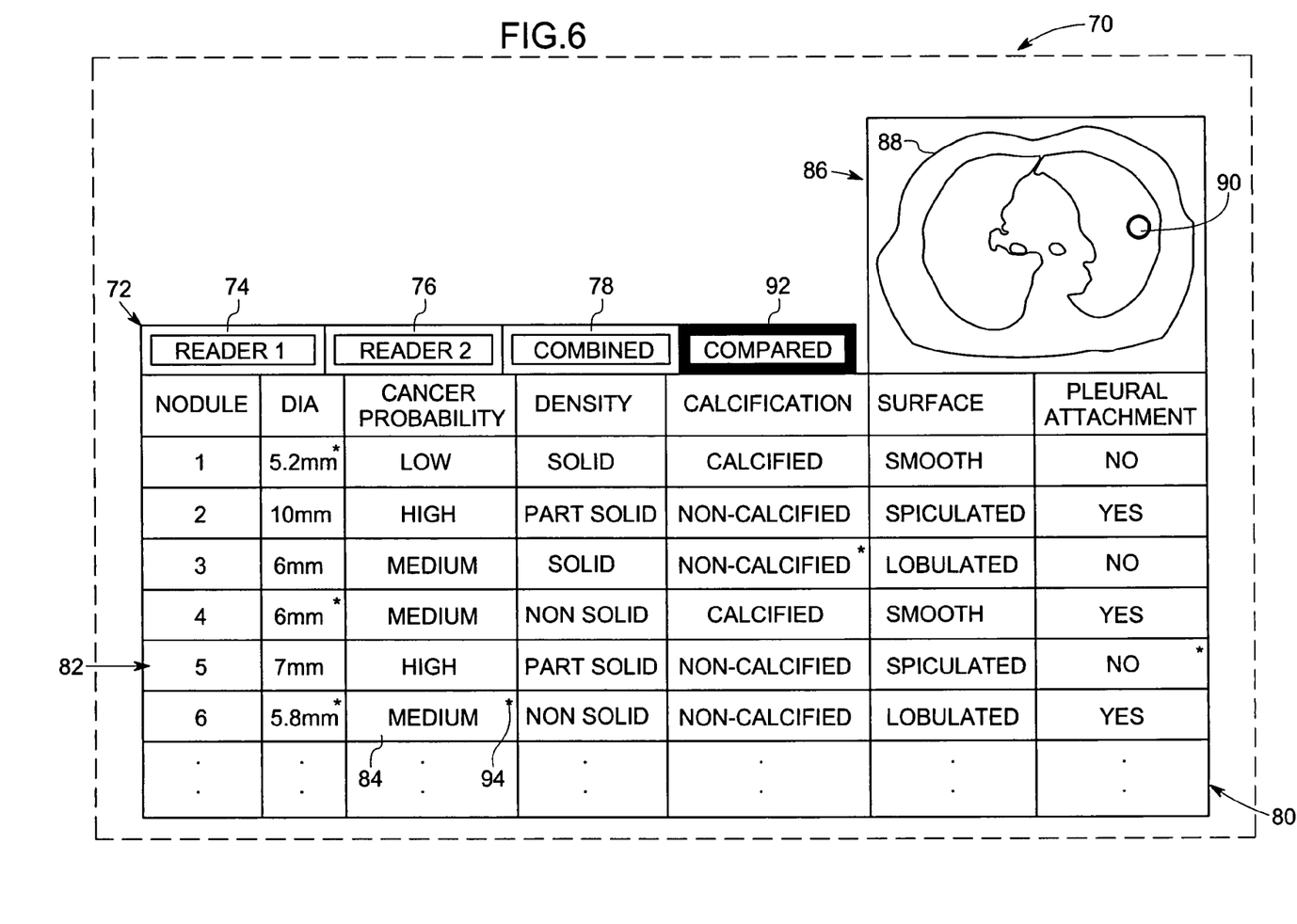
FIG. 6 depicts an exemplary user interface configured to display a comparative analysis in accordance with one aspect of the present technique.

Furthermore, a comparative analysis may be provided, such as by another selectable tab. For example, as depicted in FIG. 6, a comparative analysis is selected via "compared" tab 92. In the comparative analysis, features 82 in two or more analyses are compared, with differences indicated by a visual indicator (here denoted by asterisks 94) in the analysis. For example, the presence or absence of an identified feature 82 may be visually indicated in the comparative analysis, as might different values assigned to feature characteristics 84 in the respective analyses. As will be appreciated by those of ordinary skill in the art, the combinatorial and comparative features described herein may also be applied to combine or compare analyses performed at different times, thereby allowing a viewer to easily assess changes in a patient's condition over time.

Figure 7:
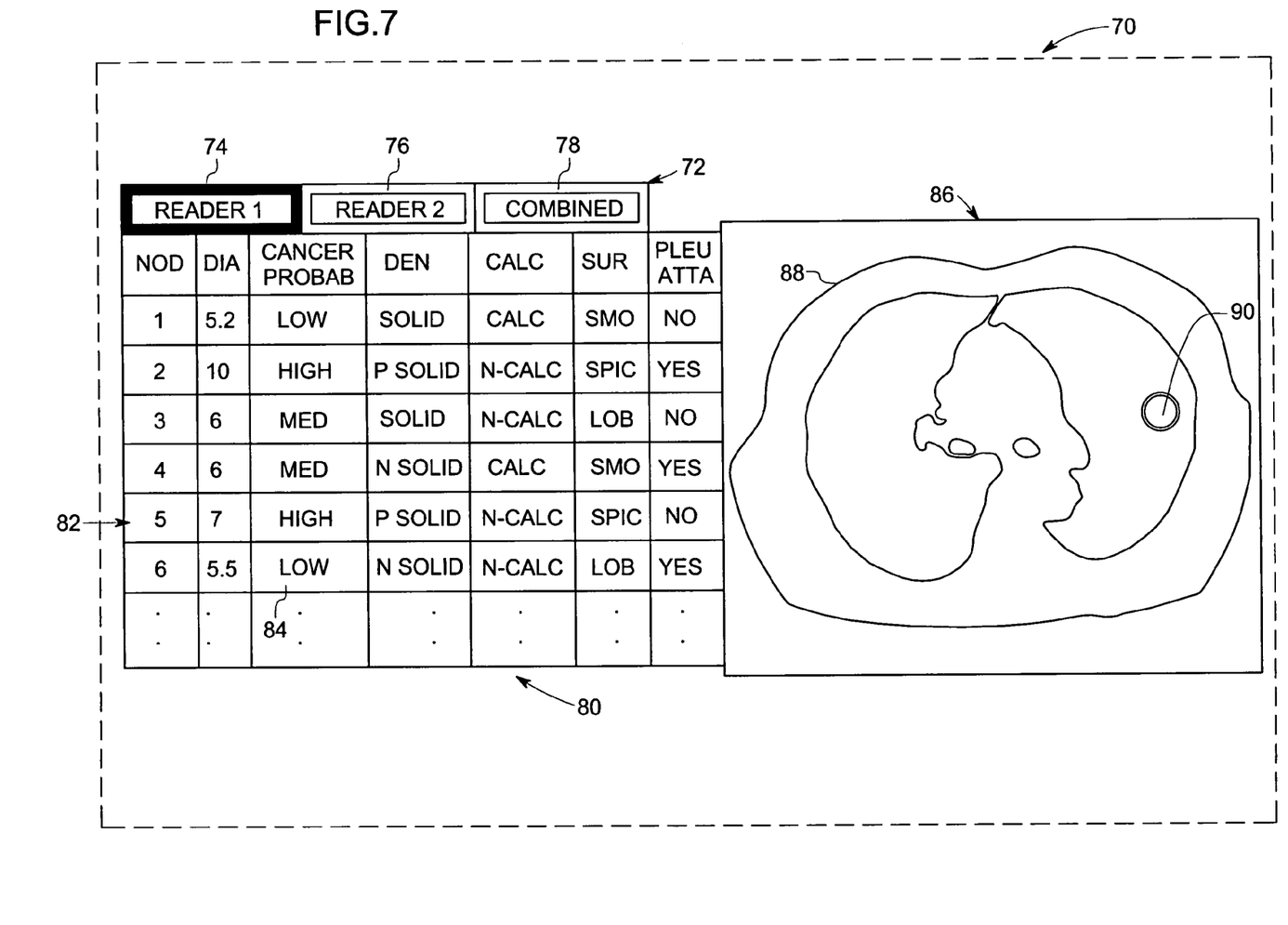
FIG. 7 depicts an alternative embodiment of the exemplary user interface of FIG. 3 configured to display an enlarged image relative to other aspects of the interface, in accordance with one aspect of the present technique.

Also, as will be appreciated by one skilled in the art, in one embodiment, the presentation of the analyses and tabs may be reduced so as to display a larger image for showing the selected feature more clearly, as illustrated in FIG. 7. This may be achieved by resizing image display region 86 or the analysis display region 80 arbitrarily or in accordance with preconfigured sizing options. Alternatively, the image display region 86 of the viewable area may be enlarged to show a larger image such that the image display region 86 overlap and/or overlies the display of the analyses.

In certain embodiments, the interaction of between the viewer and the image may be further simplified, for example, by allowing interaction between the viewer and image via a single input device, such as a mouse. In such an embodiment, the selection of an image and/or image enhancements may be accomplished via the mouse without additional inputs, such as from a keyboard. For example, a paging interface may be implemented which is controlled through the mouse. In this example, activation/deactivation of the paging control may be accomplished by clicking or clicking and holding a mouse button or by placement of the mouse in an interface region of the image. Activation of the paging control allows the viewer to navigate through the sequence of radiological images by the motion of the mouse. For example, a forward and/or rightward motion of the mouse may result in the display of subsequent axial images while a backward and/or leftward motion of the mouse may result in the display of preceding axial images.

In addition, other imaging operation such as ramp, zoom level, vari-view maximum intensity projection (MIP), and so forth may be accessible via mouse click and/or drag interactions or via other mouse functionalities, such as via a scroll wheel. Further, frequently used tools like magnification or distance measurement tools may be provided via mouse interaction with the displayed image to enhance the user convenience. For example, in one embodiment, the axial diameter of one or more nodules may be computed via successive mouse clicks at each end of the nodule diameter. Additionally, an operator can interact with the user interface for changing the viewing condition and/or performing various operations. For example, a reader such as radiologist may bookmark a feature of interest. In one embodiment, the radiologist may review the CAD found result for a particular feature and may accept or reject the data via the mouse. In another embodiment, the operator may delete the CAD or radiologist found results via the mouse. In this manner, by allowing operations such as these to be performed using only a mouse (or other input device), interaction with the interface may be simplified for the viewer, allowing more rapid and intuitive reviews of the image data.

The techniques for displaying multiple analyses of images as described in various embodiments discussed above provide a unified view of analyses performed by different readers, such as different radiologists or CAD-based results, or at different times. Further, the technique requires fewer user actions to perform review of images and one or more analyses than other techniques previously employed. Additionally, the technique provides a simple entry mechanism for radiologist found results. Further, as will be appreciated by one skilled in the art, the technique improves the workflow of the users interacting with multiple image data on a image viewing station by providing simultaneous view of readings generated via one or more readers. This makes the comparison of readings from two or more readers convenient and increases the efficiency of technologists performing comparison. It should also be noted that, the technique may improve the prediction of growth and progression of disease by comparing the results generated by one or more readers to a database of multiple patients with similar records.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for viewing image data on a display, the method comprising:
   displaying two or more selectable tabs, wherein each tab corresponds to a separate analysis of a common set of radiological images of a patient;
   displaying a selectable combined tab, wherein the combined tab corresponds to a combined presentation of two or more separate analysis of the set of radiological images of the patient;
   displaying a corresponding analysis for a selected tab, wherein the corresponding analysis comprises one or more identified features; and
   displaying a corresponding image for a selected feature, wherein the selected feature is visually indicated on the corresponding image.

2. The method of claim 1, wherein each identified feature further comprises one or more feature characteristics.

3. The method of claim 1, wherein each analysis is generated by one or more readers.

4. The method of claim 3, wherein the one or more readers comprises at least one of a radiologist, a physician, a CAD reader, or an automated algorithm.

5. The method of claim 1, wherein the analyses of the set of radiological images include a combined analysis comprising two or more separate analyses of the set of radiological images.

6. The method of claim 1, wherein displaying the corresponding image comprises enhancing the selected feature.

7. The method of claim 6, wherein enhancing the selected feature comprises at least one of enlarging a portion of the corresponding image, filtering a portion of the corresponding image, enhancing one or more image quality characteristics of the corresponding image, or differentially displaying a portion of the corresponding image.

8. The method of claim 1, wherein the selected feature is visually indicated using at least one of a color enhancement, an indicator reticle, or a circular marker.

9. The method of claim 1, further comprising interacting with the corresponding image via a mouse to alter the display of the corresponding image.

10. An image viewing station, comprising:
    a computer configured to display a user interface, the user interface comprising:
    a viewable area comprising:
    a first portion configured to display two or more selectable tabs, wherein each tab corresponds to a separate analysis of a common set of radiological images of a patient;
    a second portion configured to display a corresponding analysis for a selected tab, wherein the corresponding analysis comprises one or more identified features;
    a third portion configured to display a corresponding image for a selected feature, wherein the selected feature is visually indicated on the corresponding image; and
    a fourth portion configured to display a selectable combined tab, wherein the combined tab corresponds to a combined presentation of two or more separate analysis of the set of radiological images of the patient.

11. The image viewing station of claim 10, wherein each identified feature comprises one or more feature characteristics.

12. The image viewing station of claim 10, wherein the display areas of the first portion, the second portion and the third portion are adjustable relative to one another.

13. The image viewing station of claim 10, wherein the computer is configured to enhance the selected feature.

14. The image viewing station of claim 13, wherein the computer is configured to enhance the selected feature by at least one of enlarging a portion of the corresponding image filtering a portion of the corresponding image, enhancing one or more image quality characteristics of the corresponding image, or differentially displaying a portion of the corresponding image.

15. The image viewing station of claim 10, wherein the selected feature is visually indicated using at least one of a color enhancement, an indicator reticle, or a circular marker.

16. The image viewing station of claim 10, wherein the image viewing station is connected to an image acquisition system comprising an imager, system control circuitry, data acquisition circuitry, and data processing circuitry configured to generate the set of radiological images.

17. A user interface comprising:
    a viewable area comprising:
    a first portion configured to display two or more selectable tabs, wherein each tab corresponds to a separate analysis of a common set of radiological images of a patient:
    a second portion configured to display a corresponding analysis for a selected tab, wherein the corresponding analysis comprises one or more identified features;
    a third portion configured to display a corresponding image for a selected feature, wherein the selected feature is visually indicated on the corresponding image; and
    a fourth portion configured to display a selectable combined tab, wherein the combined tab corresponds to a combined presentation of two or more separate analysis of the set of radiological images of the patient.

18. The user interface of claim 17, wherein each identified feature comprises one or more feature characteristics.

19. The user interface of claim 17, wherein the display areas of the first portion, the second portion and the third portion are adjustable relative to one another.

20. A computer readable medium, comprising:
    code adapted to display two or more selectable tabs, wherein each tab corresponds to a separate analysis of a common set of radiological images of a patient;
    code adapted to display a selectable combined tab, wherein the combined tab corresponds to a combined presentation of two or more separate analysis of the set of radiological images of the patient;
    code adapted to display a corresponding analysis for a selected tab, wherein the corresponding analysis comprises one or more identified features; and
    code adapted to display a corresponding image for a selected feature, wherein the selected feature is visually indicated on the corresponding image.

* * * * *

UNITED STATES PATENT AND TRADEMARK OFFICE
CERTIFICATE OF CORRECTION

| | |
|---|---|
| PATENT NO. | : 7,729,523 B2 |
| APPLICATION NO. | : 11/018672 |
| DATED | : June 1, 2010 |
| INVENTOR(S) | : Hammond |

It is certified that error appears in the above-identified patent and that said Letters Patent is hereby corrected as shown below:

In Column 10, Line 13, in Claim 14, delete "image" and insert -- image, --, therefor.

In Column 10, Line 30, in Claim 17, delete "patient:" and insert -- patient; --, therefor.

Signed and Sealed this

Twenty-third Day of November, 2010

David J. Kappos
*Director of the United States Patent and Trademark Office*